United States Patent [19]

Müller et al.

[11] Patent Number: 5,624,903
[45] Date of Patent: Apr. 29, 1997

[54] PHOSPHOINOSITOL-GLYCAN-PEPTIDE WITH INSULIN-LIKE ACTION

[75] Inventors: Günter Müller, Sulzbach; Dominique Tripier, Eppstein/Taunus; Stefan Müllner, Hochheim am Main, all of Germany

[73] Assignee: Hoechst Aktiengesellschaft, Frankfurt am Main, Germany

[21] Appl. No.: 364,398

[22] Filed: Dec. 23, 1994

Related U.S. Application Data

[63] Continuation of Ser. No. 931,322, Aug. 18, 1992, abandoned.

[30] Foreign Application Priority Data

Aug. 20, 1991 [DE] Germany .................. 41 27 495.4

[51] Int. Cl.$^6$ .................................................. A61K 38/06
[52] U.S. Cl. .................... 514/18; 514/3; 514/4; 514/7; 514/8; 514/19; 530/331; 530/322; 562/561
[58] Field of Search ...................... 514/12–18, 3, 514/8; 530/321–234, 322, 303

[56] References Cited

U.S. PATENT DOCUMENTS

| | | | |
|---|---|---|---|
| 4,839,466 | 6/1989 | Saltiel | 530/395 |
| 4,906,468 | 3/1990 | Saltiel | 424/85.8 |

FOREIGN PATENT DOCUMENTS

| | | | |
|---|---|---|---|
| 0132769B1 | 2/1985 | European Pat. Off. | A61K 37/26 |
| 0132770B1 | 2/1985 | European Pat. Off. | C07K 7/40 |
| 0245956A2 | 11/1987 | European Pat. Off. | |

OTHER PUBLICATIONS

Rodel, J. Bacterial 161, 7–12, 1985.

G.Müller & W. Bandlow, "Insulin Causes Lipolytic Cleavage and Endocytosis of a cAMP–Binding Protein from Plasma Membranes in Rat Adipocytes," Biol. Chem. Hoppe–Seyler, vol. 372(9), 718–19 (1991).

P. Bruni et al., "A Phospho–Oligosaccharide Can Reduce the Stimulatory Effect of Insulin on Glycolytic Flux in Human Fibroblasts," Biochem. and Biophys. Res. Comm., vol. 166(2), 765–71 (1990).

I.Varela et al., "Role of Glycosyl–Phospatidylinositols in Insulin Signalling," NATO ASI Series, vol. H44, 167–79 (1990).

G.Müller & W.Bandlow, "A cAMP–Binding Ectoprotein in the Yeast *Saccharo–myces cerevisiae*," Biol. Abstr. 93(2):AB–242 (1992).

M.Lisanti et al., "The Distribution of Glycosyl–Phosphatidylinositol Anchored Proteins is Differentially Regulated by Serum and Insulin", Biochem. and Biophys. Res. Comm., vol. 164(2), 824–32 (1989).

W.T. Garvey, "Insulin Resistance and Noninsulin–Dependent Diabetes Mellitus: Which Horse Is Pulling the Cart?", Diabetes/Metabolism Reviews, vol. 5, No. 8, (1989), pp. 727–742.

W.L. Roberts et al, "Structural Characterization of the Glycoinositol Phospholipid Membrane Anchor of Human Erythrocyte Acetylcholinesterase by Fast Atom Bombardment Mass Spectrometry", The Journal of Biological Chemistry, vol. 263, No. 35, (1988), pp. 18776–18784.

Roberts *J. Biol Chem* 263 18776, 1988.

Garvey *Diabetes Metab Rev* 5 727, 1989.

Gunter Muller et al., "An Amphitropic cAMP–Binding Protein in Yeast Mitochondria. 1. Synergistic Control of the Intramitochondrial Location by Calcium and Phospholipid," Biochemistry, vol. 28, (1989), pp. 9957–9967.

Muller *Biochemistry* 28, 9968–9973, 1989.

Muller *Biological Chem Moppe Seylev* 372, 718, 1991.

*Primary Examiner*—David Lukton
*Attorney, Agent, or Firm*—Finnegan, Henderson, Farabow, Garrett & Dunner, L.L.P.

[57] ABSTRACT

Phosphoinositol-glycan-peptide with insulin-like action

Phosphoinositol-glycan-peptides obtainable by cleavage of adenosine 3',5'-cyclic monophosphate-binding protein, which contain glucosamine, galactose, mannose, inositol, phosphoric acid, ethanolamine and a peptide with the sequence Asx-Cys-Tyr, the preparation and use thereof for the treatment of diabetes mellitus and non-insulin-dependent diabetes are described.

7 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Glu Tyr Cys Asx
1

PHOSPHOINOSITOL-GLYCAN-PEPTIDE WITH INSULIN-LIKE ACTION

This application is a continuation of application Ser. No. 07/931,322, filed Aug. 18, 1992, now abandoned.

BACKGROUND OF THE INVENTION

The invention relates to phosphoinositol-glycan-peptides with insulin-like action, a process for the preparation thereof and the use, in particular as pharmaceutical for treating diabetes mellitus or non-insulin-dependent diabetes.

Insulin exerts a multiplicity of actions on insulin-sensitive tissue. One noteworthy effect is the rapid reduction in the glucose level in meals when insulin is administered. This is brought about by a rapid uptake of the glucose from the blood by myocytes and adipocytes. Insulin furthermore activates glycogen synthetase and inhibits lipolysis. Insulin promotes protein synthesis from amino acids and enhances the induction of pyruvate dehydrogenase and phosphofructokinase and inhibits the formation of certain enzymes of gluconeogenesis, such as pyruvate carboxylase and fructose-1,6-bisphosphatase.

Type II diabetes, non-insulin-dependent diabetes, is associated with insulin resistance by peripheral tissue such as muscle tissue or adipose tissue. The glucose utilization reduced thereby is caused by the absence of insulin stimulation of glucose transport and of subsequent metabolic processes (glycogenesis, lipogenesis). This multiple resistance suggests that there is a defect at the receptor or post-receptor level, i.e. before production of the second messenger (Garvey, Diabetes/Metabolism Reviews, 5, (1989), 727–742).

To date no active substances which bypass the insulin receptor and nevertheless display an insulin-like action have been disclosed.

DESCRIPTION OF THE PREFERRED EMBODIMENTS

It has now been found that phosphoinositol-glycanpeptides which can be obtained from adenosine 3',5'-cyclic monophosphate (cAMP)-binding protein display an insulin-like action in vitro and also display an insulin-like action on insulin-resistant tissue.

The invention therefore relates to phosphoinositol-glycan-peptides obtainable by cleavage of adenosine 3',5'-cyclic monophosphate-binding protein and/or the physiologically tolerated salts thereof.

The term insulin-resistant tissue means, for example, rat adipocytes which no longer have an active insulin receptor. cAMP-binding protein are proteins which have the property of binding adenosine 3',5'-cyclic monophosphate.

Structural data to date on the phosphoinositol-glycanpeptides according to the invention indicate a phosphoinositol which has a glycan portion which contains galactose, glucosamine and mannose, and which is coupled via a phosphorylethanolamine residue with an amide linkage to the carboxyl end of a peptide. The latter reappears within the covalently bonded glycolipids, which act as membrane anchor, in similar structure in plasma membrane proteins of higher eukaryotes (Roberts et al., J. Biol. Chem., 263, (1983), 18776–18784). The glycan residue contains glucosamine, galactose, mannose and at least two phosphate residues/mole. The peptide has the sequence Tyr-Cys-Asx and is bonded at the carboxyl end of the aspargine or aspartic acid residue via an amide linkage to the amino group of the phosphoinositol glycan. The phosphoinositol glycan portion is necessary for the activity. The peptide enhances the insulin-like action. It also emerges that an insulin-like action is shown not only by the complete phosphoinositol-glycan-peptide but also by partial structures, for example truncated peptide sequences which are bonded to the phosphoinositol glycan also show an insulin-like action or only the phosphoinositol glycan without peptide.

Examples of suitable physiologically tolerated salts of the phosphoinositol-glycan-peptide according to the invention are alkali metal, alkaline earth metal or ammonium salts, as well as those of physiologically tolerated organic ammonium or triethylamine bases.

The phosphoinositol-glycan-peptides according to the invention are prepared, for example, by a) using organisms which contain cAMP-binding protein,
b) isolating the cAMP-binding protein,
c) eliminating the protein portion from cAMP-binding protein, and purifying the resulting glycosyl-phosphatidylinositol-peptide where appropriate,
d) eliminating a mono- or diacylglycerol from the product obtained in process step c) and
e) isolating the phosphoinositol-glycan-peptide produced in process step d).

cAMP-binding protein can be obtained from numerous organisms, for example from microorganisms, plants, fungi or animal organs. Also suitable is, for example, the yeast *Saccharomyces cerevisiae*, especially DSM 6649.

The preparation of cAMP-binding protein by *Saccharomyces cerevisiae* is carried out by fermentation in a nutrient solution which contains a carbon source and a nitrogen source as well as customary inorganic salts. The cAMP-binding protein is preferentially accumulated in the plasma membrane of the yeast.

The best procedure for process step a) is as follows. The formation of cAMP-binding protein in *Saccharomyces cerevisiae* takes place well in the customary nutrient solutions for *Saccharomyces cerevisiae*. Cultivation is carried out aerobically, that is to say, for example, submerged with shaking or stirring in shaken flasks or fermenters, where appropriate introducing air or oxygen. It can be carried out in a temperature range from about 18° to 35° C. preferably at about 25° to 30° C. in particular 28° to 30° C. The pH range should be between 2 and 8, advantageously between 3 and 7. The yeast is cultivated under these conditions generally until there are about $10^7$ cells/ml of nutrient solution.

The best procedure for process step b) is such that the yeast cells are separated from the nutrient medium for the isolation of the cAMP-binding protein and are washed with buffer. Isolation takes place, for example, as described by M üller and Bandlow (Biochemistry, 28, (1989), 9957–9967). For this purpose, the yeast cells are converted enzymatically (zymolyase) into spheroplasts and comminuted with a homogenizer in the presence of protease inhibitors in the cold (0°–4° C.). Yeast lysates are centrifuged, and the cell sediment is washed with buffer and again centrifuged. The supernatants are combined and purified in a ®Percoll gradient (28% Percoll) and sucrose gradient (15 to 28% sucrose). These centrifugation steps result in cytoplasm, plasma membrane, microsomes and mitochondria being separated from one another.

The cAMP-binding protein is bound from the plasma membrane fraction, for example by an $N^6$-(2-aminoethyl)-cAMP-Sepharose column, and the cAMP-binding protein is eluted from the column with cAMP and desalted.

The best procedure for process step c) is such that the protein portion of the cAMP-binding protein is eliminated enzymatically. Used for the enzymatic cleavage are, for example, proteases such as Pronase, endoprotease Lys-C (*Lysobacter enzymogenes*) or V8 protease (Staphylococcus aureus). This achieves breakdown of the protein portion. The result with the protease V8 is a glycosyl-phosphatidylinositol with the peptide sequence Tyr-Cys-Asx; incubation with the protease Pronase yields a glycosyl-phosphatidylinositol-peptide wherein the peptide portion is composed only of the amino acid Axn.

The protease is precipitated, for example by acids such as trichloroacetic acid. The glycosyl-phosphatidylinositol-peptides are separated from the proteases by centrifugation, concentrated with a phenyl-Sepharose column and purified by thin-layer chromatography.

The best procedure for process step d) is such that the mono- or diacylglycerol residue attached to the glycosyl-phosphatidylinositol-peptide is eliminated enzymatically, and the phosphoinositol-glycan-peptide is liberated in this way. Used for the enzymatic cleavage are, for example, phospholipases such as phosphatidylinositol-specific phospholipase C (*Bacillus cereus*). This achieves elimination of the mono- or diacylglycerol residue which is bonded via the phosphate group to the myo-inositol. The glycerol-containing residue is not eliminated by the protease treatment in process step c). Process steps c) and d) can also be carried out in the reverse sequence.

The enzymatic reactions in process steps c) and d) are carried out in the presence of a detergent under conditions which are favorable for the enzymatic reaction. It is not difficult for a person skilled in the art to establish the optimal reaction conditions on the basis of the known reaction conditions for the said enzymes.

The best procedure for process step e) is such that the phospholipases are precipitated by acids such as trichloroacetic acid. The phosphoinositol-glycan-peptide is separated from the phospholipase by centrifugation, purified with a Biogel P-4 column and concentrated by thin-layer electrophoresis.

The phosphoinositol-glycan-peptides according to the invention and the physiologically tolerated salts thereof are primarily used as active substances for pharmaceutical compositions for the treatment of diabetes mellitus or non-insulin-dependent diabetes.

The invention therefore also relates to a pharmaceutical which has an effective content of phosphoinositol-glycanpeptide and/or at least one of the physiologically tolerated salts thereof in dissolved, amorphous and/or crystalline form.

The pharmaceutical is preferably a solution or suspension for injection with a pH between about 3.0 and 9.0, preferably between 5.0 and 8.5, which contains a suitable isotonicizing agent, a suitable preservative and, where appropriate, a suitable buffer, as well as, where appropriate, also a depot principle, all of course in sterile aqueous solution or suspension. The totality of the components of the composition, apart from the active substance, forms the composition vehicle.

Examples of suitable isotonicizing agents are glycerol, glucose, mannitol, NaCl, calcium or magnesium compounds such as, for example, $CaCl_2$ or $MgCl_2$.

Examples of suitable preservatives are phenol, m-cresol, benzyl alcohol and/or p-hydroxybenzoic esters.

Examples of buffer substances which can be used, especially for adjusting the pH between about 5.0 and 8.5, are sodium acetate, sodium citrate and sodium phosphate. Otherwise, physiologically acceptable dilute acids (typically HCl) or alkalis (typically NaOH) are also suitable for adjusting the pH.

It is also possible, for the purpose of altering the profile of action of the pharmaceuticals according to the invention, to admix modified (cf. EP-B- 132 769 and EP-B 132 770) and/or unmodified insulins, preferably bovine, porcine or human insulin, especially human insulin.

The pharmaceutical is prepared by converting the phosphoinositol-glycan-peptide and/or at least one of the physiologically tolerated salts thereof, where appropriate together with modified and/or unmodified insulin or derivatives thereof, with a physiologically acceptable vehicle and, where appropriate, with suitable additives and ancillary substances into a suitable dosage form.

The invention is now explained in more detail by the following examples.

EXAMPLE 1

Fermentation of *Saccharomyces cerevisiae* DSM 6649

*Saccharomyces cerevisiae* DSM is cultivated aerobically in a fermenter. The medium contains the following components in one liter of water:

| | |
|---|---|
| Yeast extract | 3 g |
| Glucose | 1 g |
| $KH_2PO_4$ | 1 g |
| $NH_4Cl$ | 1 g |
| $CaCl_2.2H_2O$ | 0.5 g |
| NaCl | 0.5 g |
| $MgSO_4.H_2O$ | 0.6 g |
| $FeCl_3$ | 0.3 ml of a 1% aqueous solution |
| Lactic acid | 22 ml of a 90% solution. |

The pH is adjusted to 5.5 with KOH. Aeration is carried out with 1 l of air per l of fermenter volume. The cells are cultured until the cell density is $1 \times 10^7$ cells/ml of culture solution; yield about 3 g wet weight per l of culture solution. The cells are harvested by centrifugation (3,000×g, 5 min) and washed with phosphate buffer, pH 6.

EXAMPLE 2

Isolation of cAMP-binding protein

The cells from Example 2 are converted enzymatically (zymolase, 2,000, Seikagaku Kogyolo, Tokyo) into spheroplasts, comminuted with a glass homogenizer (Arthur H. Thomas and Co.) at 0° C. The following isolation steps take place in the presence of protease inhibitors (phenylmethanesulfonyl fluoride (PMSF), leupeptin, aprotinin, $\alpha_2$-macroglobulin, trypsin inhibitor; Boehringer Mannheim). The cell lysate is centrifuged (1,000×g, 3 min, 4° C.), the cell sediment is washed with SEM buffer (0.25M sucrose, 0.5 mM ethylenediaminetetraacetic acid (EDTA), 20 mM 3-[N-morpholino]propanesulfonic acid (MOPS)/KOH, pH 7.4) and again centrifuged. The supernatants are combined and centrifuged (18,000×g, 15 min, 4° C.) in a ®Percoll gradient (Pharmacia, Freiburg; 28% Percoll, SEM buffer, 0.5 mg of protein/ml). Cytoplasm, plasma membrane, microsomes and mitochondria are separated from one another in this gradient. The plasma membranes float in the upper third of the gradient. They are removed from the gradient with a syringe, diluted with 5 times the volume of SEM buffer and centrifuged (48,000×g, 30 min, 4° C.). The sediment is suspended in MOPS buffer (5 mg of protein/ml) and incubated with N-[$^3$H]acetyl-concanavalin A (AmershamBuchler, Brunswick; 1 mg of protein with 55 µCi, in 500 µl of MOPS buffer (Boehringer Mannheim), 20 mM, pH 7.4, 0.5 mM EDTA, 50 mM KCl, 5 mM CaCl$_2$, 200 µg of bovine serum albumin; Behringwerke, Marburg) at 4° C. in an ultrasonic bath for 60 minutes. The binding of concanavalin A serves as marker. The suspensions are pipetted onto a sucrose gradient (15 to 28% sucrose in MOPS buffer) and centrifuged (25,000 revolutions per minute, 90 min, 4° C., BecKmann SW 27 rotor). The sucrose gradients are fractionated, and the radioactive fractions (about 23% sucrose) are combined, diluted 3-fold with a MOPS buffer (50 mMconcanavalin A; Sigma Deisenhofen, 250 mM KCl) and centrifuged (200,000×g, 60 min, 4° C., Beckmann TL-100 rotor). The sediment is washed with SEM buffer (250 mM KCl), centrifuged and resuspended in SEM buffer without KCl (2.5 mg of protein/ml).

About 500 µg of the plasma membrane proteins are solubilized in the buffer (25 mM MOPS/KOH, pH 7.0, 150 mM NaCl, 4 mM MgCl$_2$, 0.4 mM EGTA (ethylene glycol bis($\beta$-aminoethyl ether)tetraacetic acid), 0.5 mM DTT (dithiothreitol), 0.5% deoxycholate, 0.1 mM IBMX (isobutylmethylxanthine), 0.1 mM PMSF, 50 µM leupeptin, 0.1 mM aprotinin (2 mg/ml). The solution is loaded onto a 2 ml N$^6$-(2-aminoethyl)-cAMP-Sepharose column (Pharmacia, Freiburg), which has been equilibrated with the same buffer, at 4° C. The column is washed five times with 2 ml each time of buffer (25 mM MOPS/KOH, pH 7.2, 100 mM Na citrate, 5 mM DTT, 5 mM MgCl$_2$, 150 mM NaCl, 250 mM sucrose, 7.5% ethylene glycol (Merck, Darmstadt), 10% glycerol, 1 mg/ml bovine serum albumin, 1 mM IBMX). Elution is carried out at 4° C. with 2 ml of the same buffer which additionally contains 100 µM cAMP. The first 250 µl of the eluate are desalted by centrifugation of a 1 ml Sephadex G-25 column which was equilibrated with a buffer (25 mM MOPS/KOH, pH 7.0, 50 mM KCl, 5 mM MgCl$_2$, 10 mM DTT, 50 µM EDTA, 50 µM PMSF, 0.1% deoxycholate, 5% glycerol). The desalted material is incubated with the same volume of 8% polyethylene glycol 4000 (Pharmacia, Freiburg) in buffer (10 mM MOPS/KOH, pH 7.2, 1 mM EDTA) at 4° C. for 30 minutes. After centrifugation for 15 minutes, the sediment is dissolved in a buffer (20 mM MOPS/KOH, pH 7.2, 1 mM EDTA, 100 µM PMSF, 0.5% deoxycholate) (2 mg of protein/ml).

EXAMPLE 3

Preparation of phosphoglycan-peptides a) Digestion with Pronase (*Streptomyces griseus*; Boehringer Mannheim): 100 µg of cAMP-binding protein are incubated with 450 µg/ml Pronase in 1 ml of 0.1M 4-(2-hydroxyethyl)-1-piperazineethanesulfonic acid (HEPES)/KOH (pH 8.0), 15 mM CaCl$_2$, 1% Triton X-100 (Boehringer Mannheim) at 50° C. for 10 hours. After addition of 1% SDS (sodium dodecyl sulfate), the incubation is continued with a second aliquot of Pronase at 50° C. for 7 h. Automated Edmann degradation shows that Pronase degradation results in phosphoinositol glycan with amide-like linkage of asparagine to the amino end of the ethanolamine. This phosphoinositol-glycan-peptide is called PIG-N hereinafter.

b) Digestion with endoproteinase Glu-C, EC 3.4.21.19, (V8 protease) (*Staphylococcus aureus*; Boehringer Mannheim): 100 µg cAMP-binding protein are incubated with 300 µg of V8 protease in 1 ml of 20 mM (NH$_4$)$_2$CO$_3$ (pH 7.8), 0.5% octyl glucoside (Boehringer Mannheim) at 37° C. for 18 hours.

Automated Edmann degradation shows that the V8 protease digestion results in phosphoinositol glycan with the peptide tripeptide Tyr-Cys-Asx. The amino acid aspartic acid is bonded by the carboxyl terminus to the phosphoinositol glycan. The compound of phosphoinositol glycan with the tripeptide Tyr-Cys-Asx is called PIG-NCY hereinafter.

c) Digestion with endoprotease Lys-C (*Lysobacter enzymogenes*; Boehringer Mannheim): 100 µg of cAMP-binding protein are incubated with 55 µg of endoprotease Lys-C in 0.5 ml of 50 mM (NH$_4$)$_2$CO$_3$ (pH 8.2), 0.5% octyl glucoside at 37° C. for 18 hours.

Automated Edmann degradation shows that endoprotease Lys-C results in the phosphoinositol glycan with the peptide Glu-Tyr-Cys-Asx-Glu (SEQ ID NO:1). The peptide is linked to the phosphoinositol glycan via the carboxyl end of asparagine. It is called PIG-NCYE hereinafter.

d) Removal of the carboxy-terminal amino acid: Pronase-digested cAMP-binding protein (see a) is subjected to a manual Edmann degradation. The resulting phosphoinositol glycan free of amino acids is called PIG hereinafter.

After the proteolytic cleavages, the proteases are removed by precipitation with 5% trichloroacetic acid (TCA). After centrifugation (10,000×g, 15 min), the phosphoinositol-glycan-peptide derivatives contained in the supernatant, as well as the phosphoinositol glycan from the Edmann degradation, are concentrated and purified by binding to a phenyl-Sepharose column. After elution with 2% octylphenol ethylene glycol ether (TX-100) the phosphoinositol-glycan-peptide derivatives are purified by thin-layer chromatography with two different solvent systems. After the first run in an acid system (chloroform/acetone/methanol/glacial acetic acid/water 10:4:2:2:1), the phosphoinositol-glycan-peptides near the application point on a silica gel plate (type 60) are eluted with methanol and subsequently rechromatographed in a second run in a basic system (chloroform/methanol/ammonia/water 45:45:3.5:10). The phosphoinositol-glycan-peptide derivatives are again eluted from the plate (R$_f$=0.45) and extracted with chloroform/methanol (2:1). The organic phase is washed and evaporated and the material is suspended in phosphate buffer containing 0.5% TX-100.

e) The phosphoinositol glycans or phosphoinositol-glycan-peptides obtained in a) to d) are incubated with 10 units of phosphatidylinositol-specific phospholipase C, EC 3.1.1.5, (*Bacillus cereus*; Sigma, Deisenhofen) in 0.2 ml of 0.2M potassium phosphate (pH 7.2), 2 mM DTT, 10 mMMgCl$_2$, 50 mMNaCl, 0.05% TX-100 at 37° C. for 2 hours. After addition of 10 mM EDTA, the cleavage products are separated from one another by thin-layer chromatography in the basic solvent system (see d). Material in the direct vicinity of the application point is eluted from the plate and mixed with 2% poly(ethylene glycol)$_8$ mono(octylphenyl) ether) (TX-114). Phase separation is initiated by heating and centrifugation. The aqueous phase is concentrated in a Speedvac concentrator.

f) To standardize the phosphoinositol-glycan-peptides, the nitrogen of the free glucosamine in the material from process steps a) to d) is converted by permethylation into a radioactively labeled trimethylammonium cation. To do this, the sample is dried in vacuo, and 100 µl of dimethyl sulfoxide are added. After ultrasonic treatment (1 min), 10 mg of NaOH and 40 µl of methyl [$^{125}$I]iodide (0.2 µCi; NEN-Dupont, Dreieich) are added. Stirring at 25° C. for 45 minutes is followed by removal of the solvent in a Speedvac and addition of 400 µl of H$_2$O. The sample is washed three times with chloroform and the chloroform extracts are washed three times with H$_2$O. The chloroform is evaporated under N$_2$. The permethylation is linear and quantitative over a wide concentration range. In the tests for an insulin-like action, equivalent volumes (equal dpm values) of phosphoinositol-glycan-peptides are employed (1–100 arbitrary units).

g) Incubation of the material obtained in a) to d) with nitrous acid leads to cleavage of the phosphoinositol glycan.

EXAMPLE 4

Structural features of the phosphoinositol-glycan-peptides a) Yeast cells are cultured as shown in Example 1 in the presence of radioactively labeled substrates (supplied by NEN-Dupont, Dreieich):
stearic acid
myo-inositol
ethanolamine
glucosamine or
mannose.

The complete plasma membrane fraction or the cAMP-binding protein purified by affinity chromatography (see Example 2) is subjected to an SDS polyacrylamide gel electrophoresis. Staining with Coomassie blue or autoradiography of the components shows that all the abovementioned radioactive components are incorporated into the phosphoinositol-glycan-peptide.

b) The phosphoinositol-glycan-peptide obtainable as in Example 3a) is further cleaved chemically and enzymatically. The cleavage products are analysed by thin-layer chromatography and measurement of the radioactivity distribution ([$^3$H]stearic acid and [$^{14}$C]myo-inositol). The remaining radioactively labeled structure is eluted from the plate and subjected to the next cleavage reaction. Deamination with nitrous acid of the structure produced after Pronase digestion liberates phosphatidylinositol (PI). The latter is converted by phospholipase D into phosphatidic acid or by phospholipase C into diacylglycerol. This involves loss of the myo-inositol label but the radioactive labeling by stearic acid is retained. The phosphatidic acid is subsequently converted by acetolysis into diglyceride acetate. Finally, stearic acid is liberated by alkaline hydrolysis from the latter structure as well as from the diacylglycerol.

c) The structure obtained as in Example 3a) and 3e) is dried and treated with HF (60% in water, 0° C., 16 hours), and the resulting oligosaccharides are hydrolysed with 2M trifluoroacetic acid (100° C. 4 hours) The reaction solution is subsequently dried, and the sugars which are present are reduced (1% NaBH$_4$, in 0.1M ammonium hydroxide, 37° C., 1 hour) and finally acetylated (1:1 mixture of pyridine and acetic anhydride, 60° C., 1 hour). The gas chromatography is carried out with a Packard gas chromatograph, model 428; column 100/120 Supelcoport (Supelco, Bellefonte, USA) at 60° C. The following qualitative composition emerged:
mannose, galactose, myo-inositol and glucosamine.

d) The structure obtained as in Example 3a) and 3e) was hydrolysed as in c) with RF (60% in water) and 4M HCl at 100° C. for 16 hours. Separation in an amino-acid analyzer (Biotronic, LC 6001) revealed the following components:
aspartic acid, NH$_3$, ethanolamine and glucosamine.

In view of the hydrolysis conditions, the ratio of aspartic acid and NH$_3$, and the results in Example 3a), an amino acid present in the native phosphoinositol-glycan-peptide is asparagine.

EXAMPLE 5

The biological activity of the phosphoinositol-glycanpeptides (PGP) according to the invention is determined using adipocytes and pieces of diaphragm isolated by dissection from the rat.

The term "PIG" means phosphoinositol glycan without peptide, obtained as in Example 3d) and 3e); "PIG-B" means phosphoinositol glycan with asparagine or aspartic acid, obtained as in Example 3a) and 3e); "PIG-BCY" means phosphoinositol glycan with the peptide Tyr-Cys-Asx, obtained as in Example 3b) and 3e); "PIG-BCYE" means phosphoinositol glycan with the peptide Glu-Tyr-Cys-Asx (SEQ ID NO:1), obtained as in Example 3c) and 3e); "PIG-BCY (na)" means material obtained as in Example 3b) and 3e) which has been cleaved with nitrous acid (see Example 3g). The term "basal" stands for activity without stimulation, insulin stands for human insulin and dpm stands for radioactive disintegrations per minute.

The preparation of adipocytes from the rat was carried out as follows:
Adipose tissue from the epididymis (Wistar rat, 160–180 g, no feed restriction) is digested with collagenase, and the resulting isolated adipocytes are washed several times by flotation.

Preparation of pieces of diaphragm from the rat:
Small pieces of tissue (5 mm diameter) were punched out of hemidiaphragms (Wistar rat, 60–70 g, no feed restriction) and washed several times.

To inactivate the insulin receptor in rat adipocytes, the cells are treated with 10 to 40 µg/ml trypsin. After addition of protease inhibitors, the cells are washed twice by flotation, and incubation is continued at 37° C. for 15 min. These cells are then used for the test of stimulation of lipogenesis by the phosphoinositol-glycanpeptides. A control incubation with insulin shows that the trypsin-treated cells display only very little lipogenesis which can be stimulated by insulin, and thus only a very limited number of functional insulin receptors.

To inactivate the insulin receptor in rat diaphragm, the pieces of tissue are incubated in KRH buffer (0.1 mM glucose in the presence of 50 µg/ml tetradecanoylphorbol acetate) at 25° C., passing $O_2$ through continuously, for 90 min. The pieces of tissue are subsequently washed twice with KRH buffer and used for the relevant tests.

The experimental results obtained in the following experiments with tissue or cells in which the insulin receptor has been inactivated are indicated in parentheses in each case. In none of the following tests did PIG-BCYE show an effect.

a) Glycogenesis

This test determines the glycogen synthesis which can be stimulated by insulin in myocytes and which embraces glucose transport through the plasma membrane and the conversion of the glucose into glycogen including the functional insulin signal transmission cascade.

Pieces of diaphragm are incubated with 50 µM D-[U-$^{14}$C] glucose in KRH buffer in the presence or absence of insulin and PGP at 37° C. for 15 min. The medium is removed by aspiration and then the pieces of tissue are thoroughly washed, frozen at −70° C. and subsequently homogenized in a Polytron homogenizer at 2° C. The homogenate is centrifuged (2,000 g) and the supernatant is pipetted onto filter paper. To determine the glycogen formed, the filters are transferred into TCA (5%), washed with ethanol and acetone and dried, and their radio-activity is determined by scintillation measurement ([$^{14}$C]glycogen [dpm*$10^{-3}$]). The units for the phosphoinositol-glycan-peptides are arbitrary units defined as in Example 3f).

Table 1 shows the results:

TABLE 1

| | Glycogenesis [dpm · $10^{-3}$] | | | | |
|---|---|---|---|---|---|
| | Basal | Insulin | PIG | PIG-B | PIG-BCY | PIG-BCY (na) |
| | 3.3(3.4) | | | | | |
| 10 nM | | 8.4(4.1) | | | | |
| 1 | | | 3.2(3.1) | | | |
| 5 | | | 3.6(3.5) | | | |
| 25 | | | 4.4(3.9) | | | |
| 100 | | | | | | |
| 1 | | | | 3.0(2.5) | | |
| 10 | | | | 4.2(3.8) | | |
| 100 | | | | 6.7(7.2) | | |
| 1 | | | | | 3.2(2.7) | |
| 5 | | | | | 4.8(4.3) | |
| 25 | | | | | 6.5(5.8) | |
| 100 | | | | | 8.0(7.1) | |
| 1 | | | | | | 3.0(2.5) |
| 10 | | | | | | 3.2(2.9) |
| 100 | | | | | | 3.6(3.4) | b) Glycogen synthesis

The test determines the conversion, which can be stimulated by insulin, of activated glucose (UDP-glucose) into glycogen (glycogen synthase activity) including a functional insulin signal transmission cascade. Glucose transport and activation of glucose are bypassed (which differs from the glycogen synthesis measurement, see a)).

Pieces of diaphragm are incubated with D-glucose (0.1 mM) in the presence or absence of insulin and PGP at 37° C. for 30 min. A homogenate is prepared and centrifuged (20,000×g). The supernatant is incubated with U-[$^{14}$C]UDP-glucose (0.3 mM) in the presence of either 0.1 mM or 10 mM glucose 6-phosphate at 37° C. for 60 min. The mixtures are transferred to filter paper, and the filters are treated as above. The glycogen synthase activity is calculated as the fractional ratio between the I form of the enzyme (independent of glucose 6-phosphate, dephosphorylated, corresponds to the amount of active enzyme in the homogenate) and the D form of the enzyme (dependent on glucose 6-phosphate, phosphorylated, corresponds to the total amount of activatable enzyme in the homogenate) ([$^{14}$C]glycogen [dpm*$10^{-3}$]).

Table 2 shows the results:

TABLE 2

| | Glycogen synthase [dpm · $10^{-3}$] | | | | |
|---|---|---|---|---|---|
| | Basal | Insulin | PIG | PIG-B | PIG-BCY | PIG-BCY (na) |
| | 4.4(3.5) | | | | | |
| 10 nM | | 10.1(6.0) | | | | |
| 1 | | | 3.9(3.5) | | | |
| 5 | | | 4.8(3.8) | | | |
| 25 | | | 5.7(4.5) | | | |
| 100 | | | 6.7(6.0) | | | |
| 1 | | | | 3.9(3.5) | | |
| 10 | | | | 5.7(5.0) | | |
| 100 | | | | 7.6(6.2) | | |
| 1 | | | | | 3.8(3.4) | |
| 5 | | | | | 5.7(5.1) | |
| 25 | | | | | 7.2(6.4) | |
| 100 | | | | | 8.8(8.1) | |
| 1 | | | | | | 3.2(3.0) |
| 10 | | | | | | 4.0(3.5) |
| 100 | | | | | | 4.5(4.0) | c) Lipogenesis

This test determines the conversion, which can be stimulated by insulin, of glucose into toluene-soluble products (triglycerides, phospholipids, fatty acids), which requires glucose transport and triglyceride (glycerol 3-P synthesis, esterification)/phospholipid/fatty acid synthesis including the insulin signal transmission cascade.

Rat adipocytes are incubated in KRH buffer with D-[3-$^3$H]glucose (0.2 mM or 1 mM final concentration) in the presence or absence of insulin and PGP at 37° C. for 90 min. The cells are disrupted by adding a toluene-soluble scintillation cocktail, and the lipids are separated from water-soluble products and the incubation medium. After phase separation, the radioactivity incorporated in lipids is determined by scintillation measurement directly without removing the aqueous phase ([$^3$H]lipid [dpm*$10^{-3}$]).

Table 3 shows the results:

TABLE 3

| | Lipogenesis [dpm*10$^{-3}$] | | | | |
|---|---|---|---|---|---|
| Basal | Insulin | PIG | PIG-B | PIG-BCY | PIG-BCY (na) |
| 1.0(1.0) | | | | | |
| 10 nM | 11.2(1.9) | | | | |
| 1 | | 1.0(0.9) | | | |
| 5 | | 2.1(1.5) | | | |
| 25 | | 3.1(3.0) | | | |
| 100 | | 4.2(3.5) | | | |
| 1 | | | 1.0(1.2) | | |
| 10 | | | 3.5(3.3) | | |
| 100 | | | 5.4(4.8) | | |
| 1 | | | | 1.0(0.9) | |
| 5 | | | | 3.5(3.0) | |
| 25 | | | | 5.5(5.2) | |
| 100 | | | | 6.8(5.9) | |
| 1 | | | | | 1.0(0.9) |
| 10 | | | | | 1.0(1.5) |
| 100 | | | | | 2.1(2.5) | d) Intrinsic glucose transport activity

Isolated plasma membrane vesicles are obtained from rat adipocytes (see Example 5) by the adipocytes being washed twice in homogenization buffer (20 mM tris (hydroxymethyl)aminomethane (Tris)/HCl, pH 7.4, 1 mMEDTA, 0.25M sucrose) and then homogenized in 20 ml of the same buffer at 4° C. (glass homogenizer with Teflon pestle).

The homgenate is centrifuged (16,000×g, 15 min), and the sediment is suspended in the same buffer and centrifuged again. The sediment is suspended in 5 ml of homogenization buffer and layered onto a sucrose cushion (1.12M sucrose, 20 mM Tris/HCl, pH 7.4, 1 mM EDTA) and, after centrifugation (100,000×g, 70 min), the interphase with the plasma membrane vesicles is removed with a syringe, diluted with 45 ml of buffer and centrifuged again (48,000×g, 45 min). The sediment is suspended in 10 ml of buffer, centrifuged again, and suspended again in 3 ml of buffer.

Isolated plasma membrane vesicles are incubated in the presence or absence of insulin/PGP at 25° C. for 30 min. The vesicles are subsequently incubated with 50 μM D-[3-$^3$H]-glucose and L-[1-$^{14}$C]glucose of the same specific radioactivity at 25° C. for 90 sec. The mixtures are rapidly filtered off through nitrocellulose filters with suction. The filters are thoroughly washed and dried. Their radioactivity is determined by liquid scintillation measurement. The specific transport (D-[$^3$H]glucose/-L-$^{14}$C]glucose [dpm*10$^{-3}$]) is calculated as the difference between the [$^3$H] radioactivity and [$^{14}$C] radioactivity.

Table 4 shows the results:

TABLE 4

| | Intrinsic glucose transport | | | | |
|---|---|---|---|---|---|
| Basal | Insulin | PIG | PIG-B | PIG-BCY | PIG-BCY (na) |
| 2.4(2.6) | | | | | |
| 10 nM | 2.5(2.3) | | | | |
| 1 | | 2.3(2.5) | | | |
| 5 | | 2.9(2.7) | | | |
| 25 | | 2.7(2.7) | | | |
| 100 | | 2.9(3.3) | | | |
| 1 | | | 2.7(2.6) | | |
| 10 | | | 3.5(3.7) | | |
| 100 | | | 4.0(3.8) | | |
| 1 | | | | 2.3(2.7) | |
| 5 | | | | 3.5(3.7) | |
| 25 | | | | 4.7(4.6) | |
| 100 | | | | 6.9(5.8) | |
| 1 | | | | | 2.5(2.3) |
| 10 | | | | | 2.6(2.7) |
| 100 | | | | | 2.7(3.0) | e) Protein synthesis

The stimulation of protein synthesis differs from the metabolic effects of insulin measured in the previous determinations in that it belongs to the long-term actions of insulin (as growth hormone). The assay includes the insulin signal cascade.

Rat adipocytes are incubated in primary culture in Dulbecco's modified essential medium (DMEM) deplete in leucine with 50 μM L-[$^3$H]-leucine in the presence of insulin and PGP at 37° C. for 4 hours. The cells are separated from the surrounding medium by the oil centrifugation technique and mixed with water-compatible scintillation cocktail. After centrifugation, the protein precipitate is washed with acetone, suspended in 1% SDS and mixed with scintillation cocktail. The cell-associated radioactivity, determined by scintillation measurement, serves as a measure of the protein synthesis and the amino-acid transport through the plasma membrane ([$^3$H]leucine [dpm*10$^{-4}$]).

Table 5 shows the results:

TABLE 5

| | Protein synthesis | | | | |
|---|---|---|---|---|---|
| Basal | Insulin | PIG | PIG-B | PIG-BCY | PIG-BCY (na) |
| 3.5(3.4) | | | | | |
| 10 nM | 10.1(4.0) | | | | |
| 1 | | 3.5(3.3) | | | |
| 5 | | 3.55(3.5) | | | |
| 25 | | 4.0(3.5) | | | |
| 100 | | 3.8(3.3) | | | |
| 1 | | | 3.4(3.3) | | |
| 10 | | | 4.1(3.2) | | |
| 100 | | | 5.3(4.2) | | |
| 1 | | | | 3.8(3.7) | |
| 5 | | | | 4.4(4.2) | |
| 25 | | | | 5.1(5.0) | |
| 100 | | | | 6.9(5.8) | |
| 1 | | | | | 3.7(3.5) |
| 10 | | | | | 3.8(3.7) |
| 100 | | | | | 4.1(3.8) |

We claim:

1. A compound consisting of an amino acid or tripeptide residue to which is covalently bonded a phosphoinositol glycan moiety, wherein said compound is obtained by protease and phospholipase digestion of a cAMP binding protein, and wherein said compound displays one or more oi the bioiogical activities exhibited by insulin; or a pharmaceuLicaily acceptable salt thereof.

2. A compound according to claim 1 wherein said tripeptide is Tyr-Cys-Asx, and wherein said phosphoinositol glycan moiety contains at least. one of each of the following residues: glucosamine, galactose, mannose, myoinositol, phosphoric acid and ethanolamine.

3. A compound according to claim 1 wherein said amino acid residue is asparaginyl.

4. A pharmaceutical composition for the treatment of diabetes meilitus or non-insulin-dependent diabetes comprising a compound according to claim 1 and a pharmaceutically acceptable carrier.

5. A pharmaceutical composition according to claim 4 further comprising insulin in an amount effective to stimulate glycogenesis.

6. A pharmaceutical composition according to claim 5 wherein said insulin is selected from bovine insulin, porcine insulin and human insulin.

7. A method for the treatment of diabetes mellitus or non-insulin-dependent diabetes in a patient comprising the step of administering to said patient an effective amount of the pharmaceutical composition as recited in claim 4.

* * * * *

UNITED STATES PATENT AND TRADEMARK OFFICE
CERTIFICATE OF CORRECTION

PATENT NO. : 5,624,903
DATED : April 29, 1997
INVENTOR(S) : Guenter MUELLER et al.

It is certified that error appears in the above-indentified patent and that said Letters Patent is hereby corrected as shown below:

On the Title page, Item [73], in the Assignee, line 1, "Heochst" should read --Hoechst--.

In Claim 1, Col. 13, line 27, "oi" should read --of--.

In Claim 1, Col. 13, lines 28-29, "pharmaceuLicaily" should read --pharmaceutically--.

In Claim 2, Col. 13, line 32, "least." should read --least--.

In Claim 4, Col. 14, line 23, "meilitus" should read --mellitus--

Signed and Sealed this

Third Day of February, 1998

Attest:

BRUCE LEHMAN

*Attesting Officer*     *Commissioner of Patents and Trademarks*